United States Patent [19]
Schulte

[11] Patent Number: 5,763,886
[45] Date of Patent: Jun. 9, 1998

[54] TWO-DIMENSIONAL IMAGING BACKSCATTER PROBE

[75] Inventor: Robert L. Schulte, Port Washington, N.Y.

[73] Assignee: Northrop Grumman Corporation, Los Angeles, Calif.

[21] Appl. No.: 695,244

[22] Filed: Aug. 7, 1996

[51] Int. Cl.⁶ .................. G01N 23/203; G01N 23/10
[52] U.S. Cl. ........................... 250/358.1; 378/57
[58] Field of Search ................ 250/358.1; 378/57, 378/53, 90, 88

[56] References Cited

U.S. PATENT DOCUMENTS 5,600,303  2/1997  Husseiny et al. .................. 378/57
5,600,700  2/1997  Krug et al. ........................ 378/57

*Primary Examiner*—Michael J. Tokar
*Assistant Examiner*—Richard Hanig
*Attorney, Agent, or Firm*—Terry J. Anderson; Karl J. Hoch, Jr.

[57] ABSTRACT

A two-dimensional imaging backscatter probe has a radiation source, a radiation detector, and a position sensing device to which the radiation detector is attached. A mapping circuit generates a two-dimensional map of backscattered radiation as a function of position of the radiation detector. A display displays the two-dimensional map. The two-dimensional imaging backscatter probe of the present invention facilitates non-destructive/non-intrusive inspection of a test article for contraband and/or structural integrity inspection.

21 Claims, 4 Drawing Sheets

Fig. 4
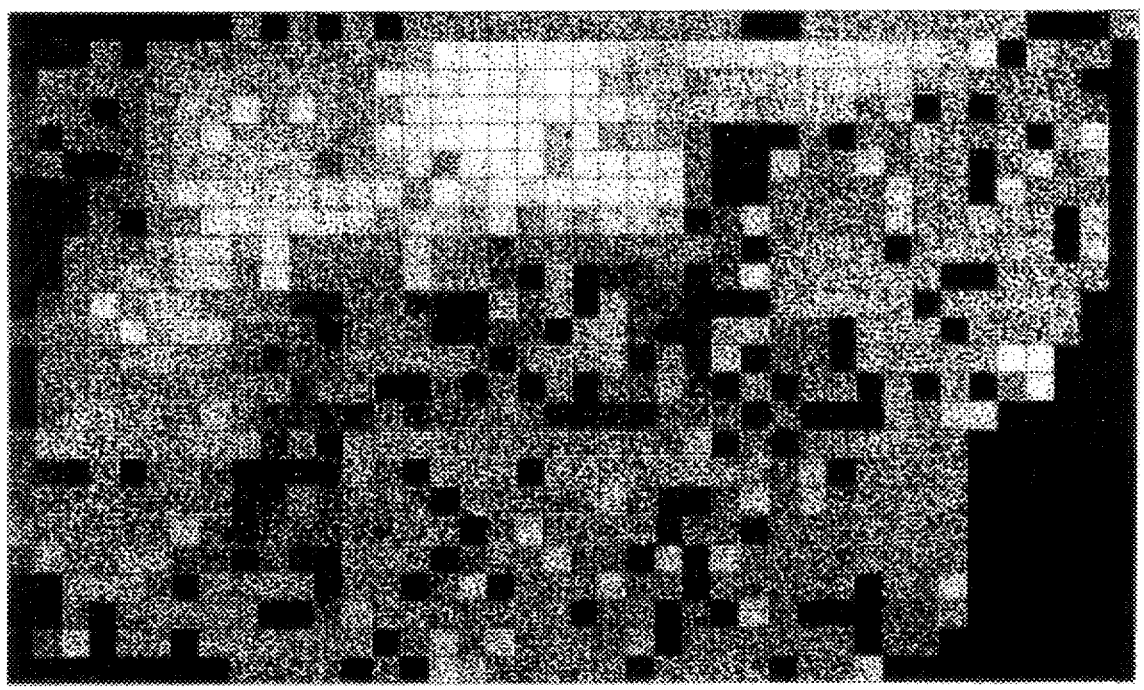
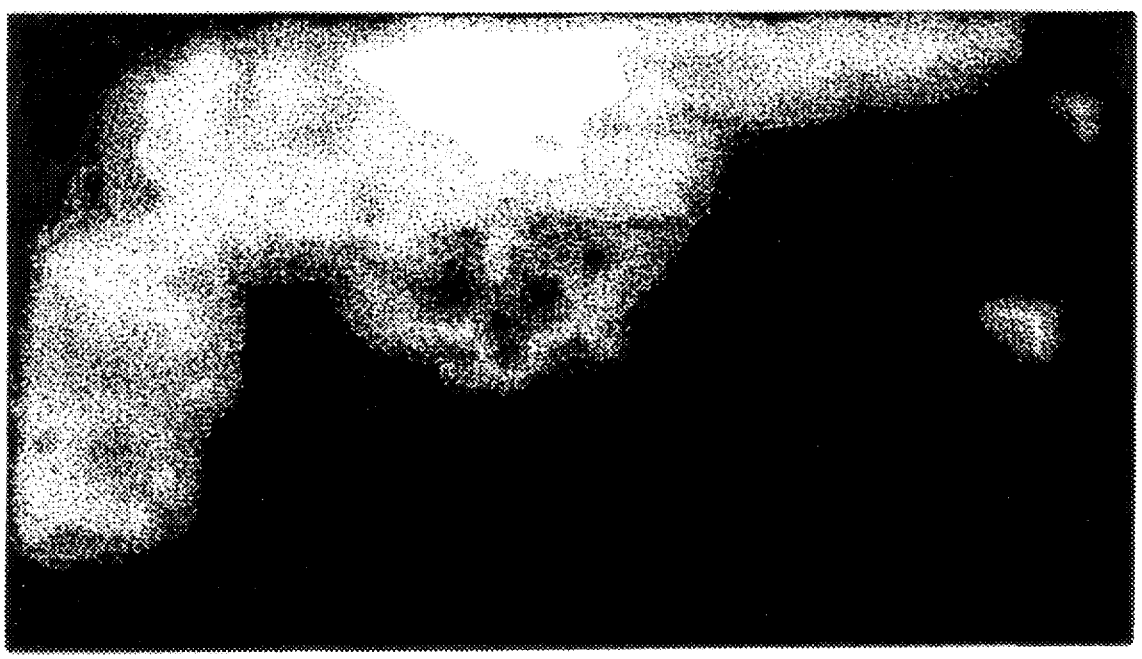
Fig. 5

TWO-DIMENSIONAL IMAGING BACKSCATTER PROBE

FIELD OF THE INVENTION

The present invention relates generally to non-destructive/non-intrusive inspection devices and more particularly to a two-dimensional imaging backscatter probe utilizing gamma radiation or the like to facilitate non-destructive/non-intrusive inspection for such applications as contraband detection.

BACKGROUND OF THE INVENTION

It is well known that various types of contraband are commonly concealed within various different solid objects which are difficult to inspect in a non-destructive/non-intrusive manner. Such contraband typically includes weapons, drugs, and/or currency, among other items. For example, it is not unusual for Customs officials at airports and various other ports of entry to discover quantities of illegal drugs contained within generally solid objects such as those comprised of wood, stone, or metal. Visual inspection would require opening or breaking apart the solid object and is therefore typically undesirable.

Further, non-intrusive and/or non-destructive inspection of various commercial products is frequently desirable. For example, such inspection is commonly performed upon aircraft in order to detect the presence of foreign objects such as water or epoxy within honeycomb structures, as well as to detect undesirable voids within structural materials.

Although various means for non-intrusively or non-destructively inspecting solid objects are known, such means are typically not portable and thus are of limited utility. Indeed, contemporary non-destructive/non-intrusive contraband detection systems, generally employing either gamma ray or X-ray detection techniques, typically are very large in scale, and generally have substantial power requirements. Thus, it is generally necessary to bring items suspected of concealing contraband to a fixed-location inspection station to facilitate the non-destructive/non-intrusive inspection thereof.

Although portable backscatter probes are known, such contemporary devices provide the operator with only very limited information regarding the scanned object. For example, it is known to sound an audio alarm or to display a count rate in response to the detection of backscattered radiation. However, such extremely rudimentary information is only of very limited use. In many instances, a visual image of a scanned object is necessary for the accurate identification thereof. Thus, the audio alarm or count rate display provided by such contemporary devices is not adequate for the reliable and accurate identification of contraband. Therefore, in many instances, such contraband goes undetected.

Several different non-destructive/non-intrusive inspection techniques have been developed to perform thickness measurements, flaw detection, or sub-surface characterization. Such contemporary methodologies exploit a variety of different phenomenon including ultrasonics, eddy currents, and microwaves, as well as electrical and magnetic fields. However, each of these contemporary technologies suffers from inherent deficiencies which limit the detection of cavities and hidden recesses in many of the types of material which are commonly encountered during routine inspection operations.

One important problem with the use of ultrasonics is the difficulty in scanning large areas while maintaining continuous mechanical coupling of the transducer with the inspection surface. Furthermore, many common materials, such as wood or cardboard, are not suitable for conventional ultrasonic gauging.

Inherent limitations of the eddy current method include the requirement for a conductive surface and the fact that inspection results are easily influenced by many material variations which frequently lead to ambiguous test results.

The use of detectors which are based upon microwave phenomenon are also commercially available. However, such devices are unable to penetrate deeply into conductors, i.e., metals. Thus, non-metallic materials within a metal enclosure such as an automobile door panel, simply cannot be sensed by such microwave detectors.

The main disadvantage of electromagnetic probes which utilize the electric current technique is that the specimen must be conductive. Also, such devices must be capable of measuring very small potentials. Edge effects and calibration complications also limit the accuracy of such contemporary methodology. Similarly, for magnetic probes, the inspection is limited to items having ferromagnetic materials present within the specimen being probed.

Thus, while such contemporary methodologies are frequently suitable for certain specific non-destructive/non-intrusive inspection applications, none of these contemporary methodologies possess the capability and flexibility to probe all types of materials, including metal, wood, plastic, etc., which are commonly encountered during routine contraband inspections and the like. Additionally, most of the contemporary methodologies require implementation procedures, calibrations, or a level of expertise, which is not desirable for routine use in field operations.

As such, there exists an immediate need for an effective and accurate portable instrument which may be utilized in the non-destructive/non-intrusive inspection of solid objects for contraband and the like and which may also be utilized for the non-destructive/non-intrusive inspection of various commercial products for defects.

SUMMARY OF THE INVENTION

The present invention specifically addresses and alleviates the above-mentioned deficiencies associated with the prior art. More particularly, the present invention comprises a two-dimensional imaging backscatter probe comprising a radiation source and a radiation detector. The radiation source and the radiation detector preferably share a common housing and are both attached to a position sensing device which provides an output representative of the relative position of the radiation detector with respect to the object being scanned. As those skilled in the art will appreciate, the radiation source need not necessarily be co-located with the detector.

A mapping circuit generates a two-dimensional map of the radiation backscattered from the test article as a function of position of the radiation detector.

The radiation source preferably comprises a gamma radiation source, preferably a gamma radiation source utilizing approximately 100 µCi of $^{57}Co$ with primary emissions at 122 keV and 136 keV. Alternatively, an X-ray radiation source may be utilized.

The radiation detector preferably utilizes a cesium iodide scintillator crystal and a photomultiplier for amplifying the output of the cesium iodide scintillator.

The mapping circuit processes position information from the position sensing device and count rate from the radiation detector to provide a drive signal for the display. The mapping circuit preferably comprises a general purpose microprocessor, preferably a portable computer, in electrical communication with the position sensing device and the radiation detector.

These, as well as other advantages of the present invention will become more apparent from the following description and drawings. It is understood that changes in the specific structure shown and described may be made within the scope of the claims without departing from the spirit of the invention.

BRIEF DESCRIPTION OF THE DRAWINGS

FIG. 4 is a real time image of a gun (simulated with a water pistol filled with water) which is suspended ½ inch below a 1/16 inch aluminum panel; and FIG. 5 is an enhanced two-dimensional image of the gun of FIG. 4.

DETAILED DESCRIPTION OF THE PREFERRED EMBODIMENT

The detailed description set forth below in connection with the appended drawings is intended as a description of the presently preferred embodiment of the invention and is not intended to represent the only form in which the present invention may be constructed or utilized.

Figure 1:
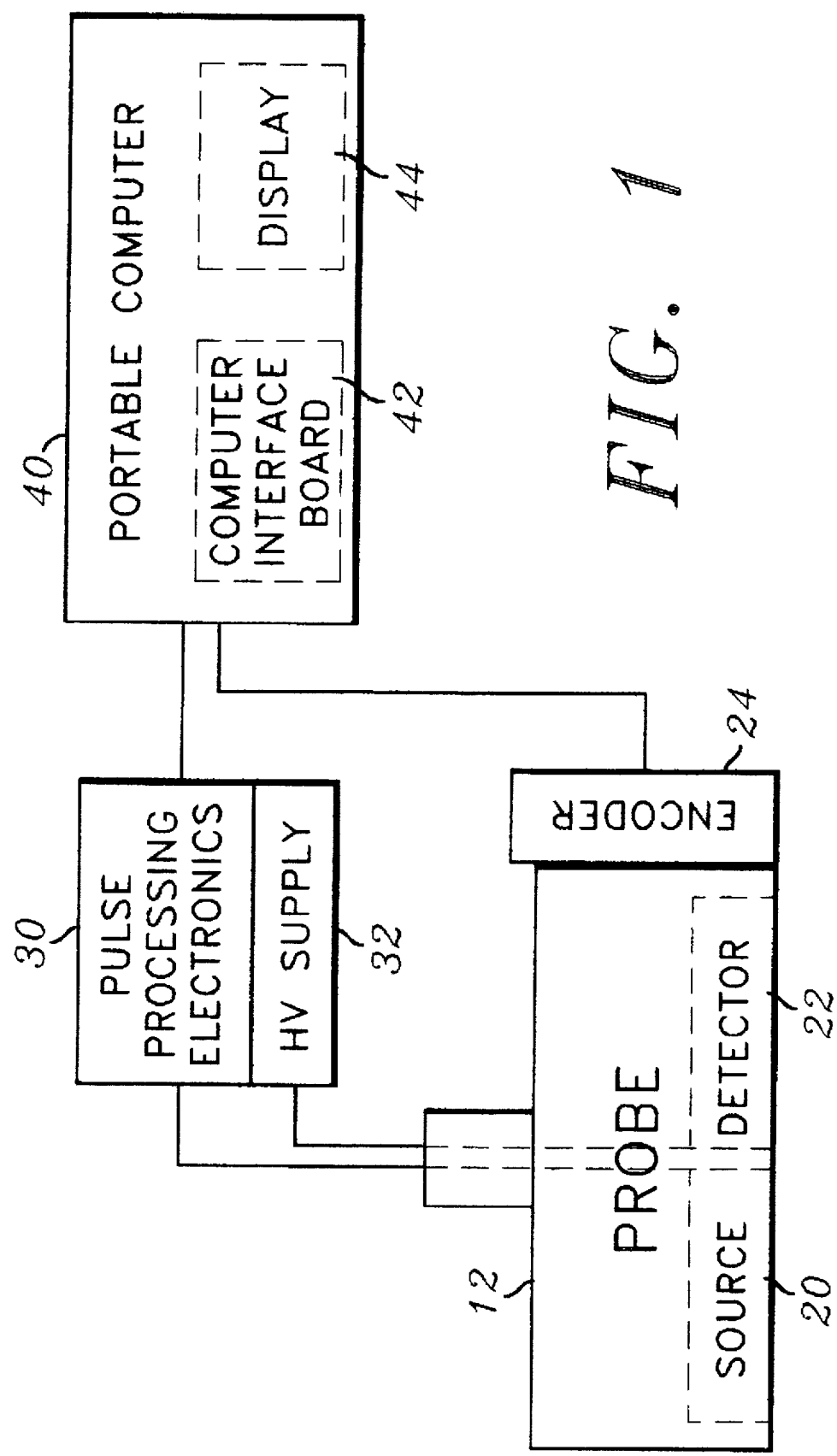
FIG. 1 is an electrical block diagram of the two-dimensional imaging backscatter probe of the present invention.
Figure 2:
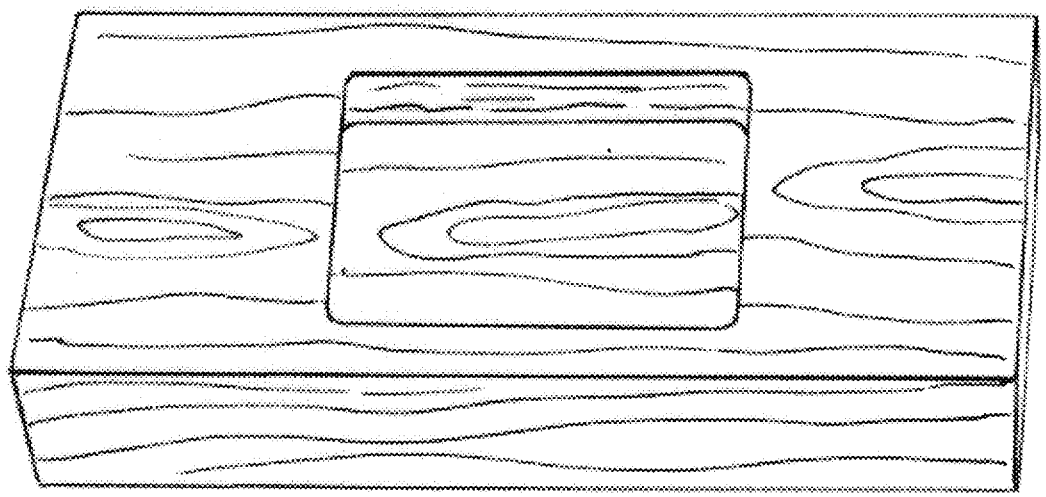
FIG. 2 is a block of wood having a cavity formed therein within which contraband, e.g., illegal drugs, may be stored.
Figure 3:
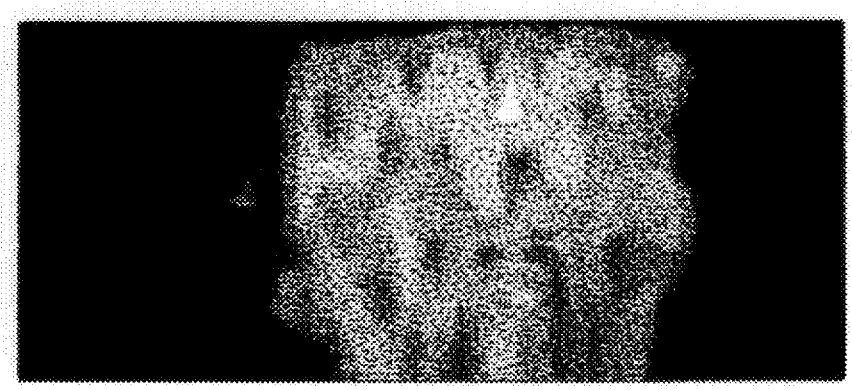
FIG. 3 is an enhanced two-dimensional image of a scan of the block of wood of FIG. 2 having a substance simulating a drug disposed within the hollow cavity thereof.
Figure 6:
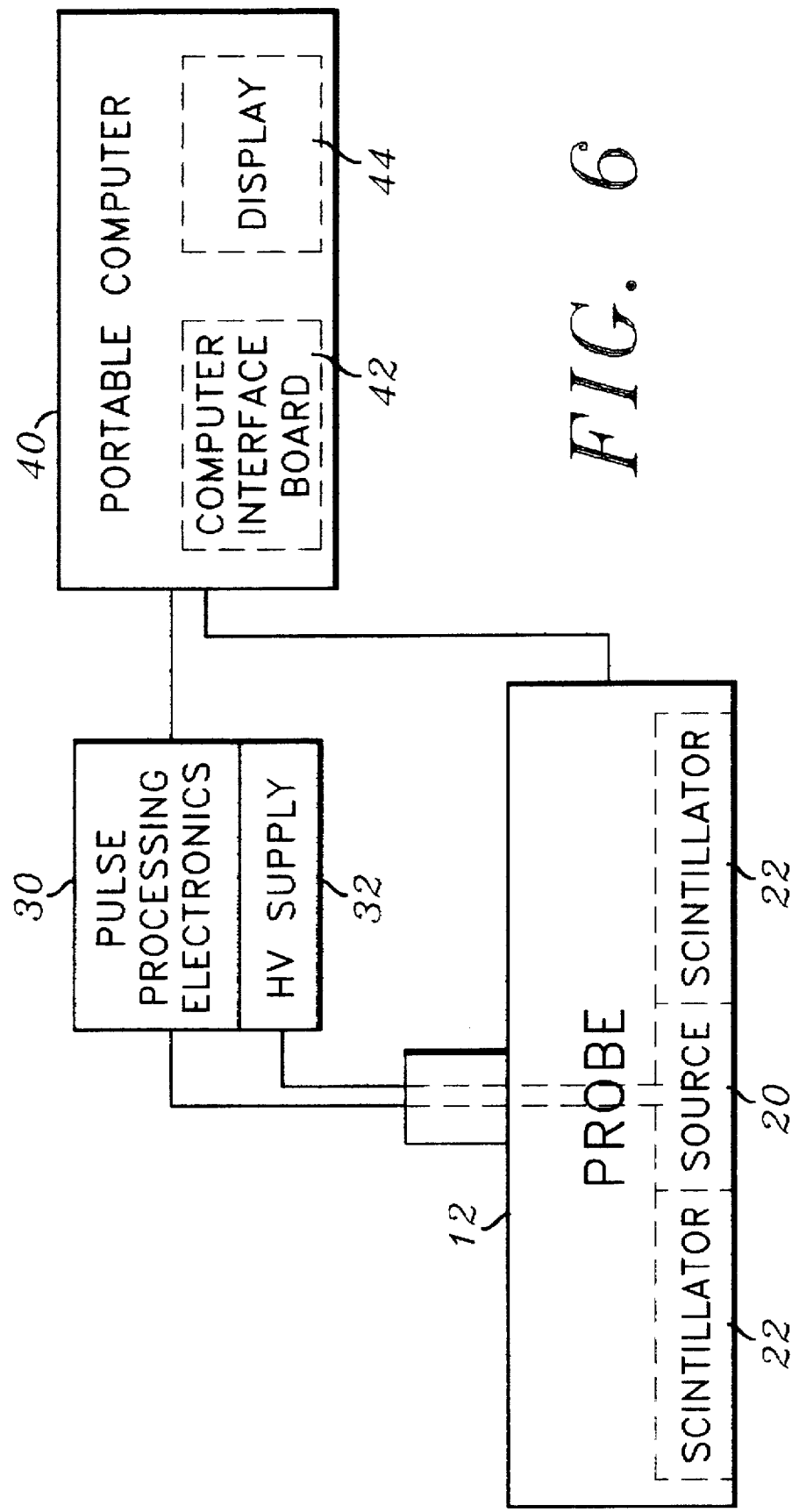
FIG. 6 is a preferred embodiment with an annular scintallator.

The two-dimensional imaging backscatter probe of the present invention is illustrated in FIG. 1, while images generated therewith are illustrated in FIGS. 3–5. FIG. 2 shows a block of wood which has been hollowed out to contain contraband.

The two-dimensional imaging backscatter probe of the present invention comprises a gamma-ray backscatter probe according to the preferred embodiment thereof. Those skilled in the art will appreciate that various other types of radiation, e.g., X-ray, are likewise suitable. As used herein, the term radiation is defined to include all such types of radiation which are suitable for use such in backscatter imaging.

Referring now to FIG. 1, the two-dimensional imaging backscatter probe generally comprises a control circuit in electrical communication with a probe assembly, preferably via a flexible cable. The probe assembly comprises a probe 12 for facilitating backscatter imaging and an encoder 24 for providing position information, as discussed in detail below. An electronics housing (not shown) preferably encloses the control circuit, which comprises all of the electronics-including the mapping circuit-necessary to form a display of the two-dimensional backscatter image. Alternatively, electrical communication may be provided from the probe assembly to a general purpose microprocessor, such as a portable computer 40, which may be utilized for the processing of the position and image data provided by the probe assembly.

Whether or not a general purpose microprocessor, e.g., portable computer, is used to process position and image data, a portable computer may be utilized to perform image enhancement, if the control circuitry contained within the electronics housing is not configured to do so.

A display 44 (FIG. 1) preferably comprises a liquid crystal display. Those skilled in the art will appreciate that various other types of displays are likewise suitable.

The probe 12 comprises a radiation source, preferably a gamma radiation source 20 and a detector, preferably a gamma radiation detector 22.

The gamma radiation source 20 preferably comprises a cobalt gamma radiation source, preferably approximately 100 µCi of $^{57}$Co with primary emissions at 122 keV and 136 keV. According to the preferred embodiment of the present invention, approximately 85% of the emissions are at 122 keV and approximately 11% of the emissions are at 136 keV. The half life of cobalt is approximately 272 days. It has been found that such a $^{57}$Co gamma radiation source is of sufficient strength to be effective for approximately 18 months.

Replacement of the gamma radiation source is preferably facilitated by providing an access plug in the probe, such that the gamma radiation source can be easily changed in the field.

The use of such a $^{57}$Co gamma radiation source is preferred since the quantity specified is exempt from licensing, as well as the consequent accountability and documentation requirements necessary for licensed radiation sources.

Attached to or formed integrally with the probe 12 is a position sensor or encoder 24. The encoder 24 preferably comprises orthogonal mechanical tracking devices, such as those of a computer mouse or track ball, so as to provide a real time output representative of the relative position (with respect to the starting position, as with a computer mouse) of the probe 12 upon a generally flat surface.

The detector 22 preferably comprises a cesium iodide (CsI) scintillator crystal which is affixed to a miniaturized photomultiplier tube. According to the preferred embodiment of the present invention, the detector 22 is annular in shape with the finely collimated gamma radiation source 20 mounted in the central hole of the scintillator crystal, collocation of the radiation source and the detector improves the backscatter signal which enhances the image quality. A high-voltage supply 32 provides the bias voltage necessary for the operation of the detector 22.

Control circuitry, preferably a portable computer 40, contains a computer interface board 42 for receiving the count rate output of the detector 22 and the position output of the encoder 24. The portable computer preferably comprises an IBM compatible computer having a Pentium or better micro-processor to facilitate rapid processing for near real time image enhancement. The pulse processing electronics 30 preferably comprises an amplifier, a single channel analyzer, and a bias voltage supply mounted upon a single circuit board drawing power from the computer power unit.

The portable computer 40 thus provides for the acquisition and analysis of the data generated by the probe 12. The detector 22 and encoder 24 output signals for processing via the computer interface board 42 within the portable computer 40, so as to generate an array containing count rate information from the detector 22 corresponding to specific locations on the scanned surface as provided by the encoder 24.

According to the preferred embodiment of the present invention, all software tasks performed by the portable computer 40 are executed under software control via pull-down menus in a Windows-like environment. In this manner, the user can post-process or enhance the images, or provide for storage of the same by simply clicking on the appropriate menu items.

Display 44 can provide either the real-time image, or the enhanced image, so as to facilitate the detection and identification of contraband and the like.

Real-time imagery is achieved through software processing of the input data representative of position and count rate so as to define each pixel element thereof. Thus, the physical scanning area is divided into individual pixel elements and the number of individual pixel elements depends upon the area to be scanned and the required position resolution. Both the starting position and the physical area of the scan are preferably input into the microprocessor. The counts accumulated by the detector 22 for each pixel element are normalized by the incremental time spent as the encoder transverses the pixel element, so as to provide an accurate count rate or frequency data. In this manner, the speed with which a manual scan is performed is compensated for such that the count rate for each pixel element does not depend upon the time taken to traverse that element.

Scanning is accomplished by holding the probe 12 against the surface to be scanned, and then moving the probe 12 in generally straight lines back and forth across the surface until the area to be scanned has been covered. During this manual scanning process, the encoder 24 provides an output which allows the portable computer 40 to associate a position with each reading of the detector 22.

The relative differences in pixel count rate, which reflect the density variations being measured, are preferably processed into a 256 level grey scale (such as that shown in FIG. 4 of the drawings). The image is constructed on a pixel-by-pixel basis as the probe is moved over the area to be scanned in a fashion similar to painting. In this manner, a substantial portion of the surface of the area to be inspected is covered by the probe.

Referring now to FIG. 2, a block of wood having a cavity formed therein is shown. As those skilled in the art will appreciate, contraband, such as illegal drugs, can be concealed within the cavity formed in the block of wood, so as to facilitate smuggling thereof.

Referring now to FIG. 3, an enhanced two-dimensional image of the block of wood shown in FIG. 2 reveals the presence of simulated drug disposed therein.

Referring now to FIG. 4, a real time image of a pistol suspended one half inch below a one sixteenth inch thick aluminum panel is shown. The real time image clearly shows the general shape of the gun.

Referring now to FIG. 5, an enhanced image of the gun of FIG. 4 is shown. In the enhanced image, the shape of the gun is much more apparent and easily recognized. Those skilled in the art will appreciate that various different image enhancement algorithms are suitable for such image processing.

The present invention thus provides the capability to probe all types of materials, including metal, wood, plastic, laminants, etc., which are commonly encountered during routine contraband inspections. Thus, the present invention is suitable for use in the scanning of a wide variety of materials and structures. The present invention does not require complex calibrations, or a level of operator expertise which is not practical for use in field operations. Thus the two-dimensional imaging backscatter probe of the present invention is simple to calibrate and use.

Although the discussion of the present invention contemplates use thereof for the detection and identification of contraband such as illegal drugs, hidden weapons, currency, etc., it is understood that the present invention may similarly be utilized to test structural components, e.g. such as those of aircraft, etc., for the presence of voids or undesirable materials. As such, discussion of the present invention for use in contraband detection and identification is by way of example only, and not by way of limitation.

It is further understood that the exemplary two-dimensional imaging backscatter probe described herein and shown in the drawings represents only a presently preferred embodiment of the invention. Indeed, various modifications and additions may be made to such embodiment without departing from the spirit and scope of the invention. For example, various different position sensing means are contemplated. For example, the position sensor may alternatively comprise an optical or ultrasound position sensor. Also, as mentioned above, various different types of radiation sources are suitable in the practice of the present invention. These and other modifications and additions may be obvious to those skilled in the art and may be implemented to adapt the present invention for use in a variety of different applications.

What is claimed is:

1. A portable two-dimensional imaging backscatter system for performing non-destructive and non-intrusive inspection of a test article, the system comprising:
   a) a radiation source for emitting radiation toward the test article;
   b) a radiation detector for sensing radiation backscattered from the test article;
   c) a position sensing device attached to the radiation detector for generating position information of the radiation detector as the radiation detector moves along the surface of the test article, the test article being at rest;
   d) a mapping circuit in electrical communication with the radiation detector and the position sensing device for generating a two-dimensional map of backscattered radiation from the test article as a function of position of the radiation detector; and
   e) a display for displaying the two-dimensional map.

2. The system as recited in claim 1 wherein the radiation source comprises a gamma radiation source.

3. The system as recited in claim 1 wherein the radiation source comprises an X-ray source.

4. The system as recited in claim 1 wherein the radiation source comprises cobalt.

5. The system as recited in claim 1 wherein the gamma radiation source comprises approximately 100 µCi of $^{57}$Co with primary emissions at 122 keV and 136 keV.

6. The system as recited in claim 1 wherein the radiation detector comprises a cesium iodide scintillator crystal and a photomultiplier.

7. The system as recited in claim 1 wherein the mapping circuit processes position information from the position sensing device and count rate from the radiation detector to provide a drive signal for the display.

8. The system as recited in claim 1 wherein the mapping circuit comprises a general purpose microprocessor.

9. The system as recited in claim 1 wherein the mapping circuit comprises a portable computer in electrical communication with the position sensing device and the radiation detector.

10. A method for performing two-dimensional measurements of backscatter from a test article, the method comprising the steps of:

a) emitting radiation from a radiation source toward the test article;

b) sensing radiation backscattered from the test article with a radiation detector;

c) sensing a plurality of positions of the radiation detector as the radiation detector is moved about the test article;

d) generating a two-dimensional map of the backscattered radiation as a function of the positions of the radiation detector as it is moved about the test article; and e) displaying the two-dimensional map upon a display.

11. The method as recited in claim 10 wherein the step of emitting radiation from a radiation source comprises emitting radiation from a gamma radiation source.

12. The method as recited in claim 10 wherein the step of emitting radiation from a radiation source comprises emitting radiation from an X-ray radiation source.

13. The method as recited in claim 10 wherein the step of emitting radiation from a radiation source comprises emitting radiation from a cobalt radiation source.

14. The method as recited in claim 10 wherein the step of emitting radiation from a radiation source comprises emitting radiation from a source comprising 100 μCi of $^{57}$Co with primary emissions at 122 keV and 136 keV.

15. The method as recited in claim 10 wherein the step of sensing radiation backscattered from the test article with a radiation detector comprises sensing radiation with a cesium iodide scintillator crystal and a photomultiplier.

16. The method as recited in claim 10 wherein the step of generating a two-dimensional map of the backscatter gamma radiation as a function of the positions of the radiation detector comprises processing position information from a position sensing device and processing count rate from the radiation detector to provide a drive signal for the display.

17. The method as recited in claim 10 wherein the step of generating a two-dimensional map of the backscattered radiation as a function of the positions of the radiation detector comprises generating a two-dimensional map via a general purpose microprocessor.

18. The method as recited in claim 10 wherein the step of generating a two-dimensional map of the backscattered radiation as a function of the positions of the radiation detector comprises generating a two-dimensional map of the backscattered radiation utilizing a portable computer which is in electrical communication with the position sensing device and the radiation detector.

19. A hand-held probe for performing non-destructive and non-intrusive inspection of a test article, the probe comprising:

a) a radiation source for emitting radiation toward the test article; and b) a radiation detector for sensing radiation backscattered from the test article, the radiation detector being a scintillator crystal having an annular shape;

wherein the radiation source is disposed in a central hole of the radiation detector such that the radiation source and the radiation detector are substantially collocated.

20. A hand-held probe for performing non-destructive and non-intrusive inspection of a test article, the probe comprising:

a) a radiation source for emitting radiation toward the test article;

b) a radiation detector for sensing radiation backscattered from the test article; and c) a position sensing device attached to the radiation detector for generating position information of the radiation detector as the radiation detector moves along the surface of the test article, the test article being at rest.

21. The hand-help probe as recited in claim 20 wherein the position sensing device comprises an orthogonal mechanical tracking device.

* * * * *